United States Patent
Hoshino et al.

(10) Patent No.: US 7,351,564 B2
(45) Date of Patent: Apr. 1, 2008

(54) SQS GENE

(75) Inventors: Tatsuo Hoshino, Kamakura (JP);
Kazuyuki Ojima, Kanagawa-ken (JP);
Yutaka Setoguchi, Kanagawa-ken (JP)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/528,872

(22) PCT Filed: Sep. 23, 2003

(86) PCT No.: PCT/EP03/10573

§ 371 (c)(1),
(2), (4) Date: Sep. 29, 2005

(87) PCT Pub. No.: WO2004/029255

PCT Pub. Date: Apr. 8, 2004

(65) Prior Publication Data

US 2006/0160172 A1    Jul. 20, 2006

(30) Foreign Application Priority Data

Sep. 27, 2002 (EP) .................. 02021619

(51) Int. Cl.
*C12N 15/82* (2006.01)
*C12N 9/18* (2006.01)
*C12N 5/04* (2006.01)
*C07H 21/04* (2006.01)

(52) U.S. Cl. ............... 435/193; 435/69.1; 435/254.21; 435/255.2; 435/320.1; 435/440; 435/252.3; 435/252.33; 536/23.2

(58) Field of Classification Search .............. None
See application file for complete search history.

(56) References Cited

U.S. PATENT DOCUMENTS 5,182,208 A    1/1993    Johnson et al.

FOREIGN PATENT DOCUMENTS

WO    WO 96/09393    3/1996
WO    WO 00/01650    1/2000

OTHER PUBLICATIONS

Misawa and Shimada, "Metabolic Engineering For the Production of Carotenoids in Non-Carotenogenic Bacteria and Yeasts," *Journal of Biotechnology*, vol. 59, pp. 169-181 (1998).
Robinson, G.W. et al., "Conservation Between Human and Fungal Squalene Synthetases: Similarities in Structure, Function, and Regulation," *Molecular and Cellular Biology*, vol. 13, No. 5, pp. 2706-2717 (1993).
Shimada, H. et al., "Increased Carotenoid Production by the Food Yeast Candida Utilis through Metabolic Engineering of the Isoprenoid Pathway," *Applied and Environmental Microbiology*, vol. 64, No. 7, pp. 2676-2680 (1998).
Corran, A.J., "*Squalene Synthase in Plant Pathogenic Fungi*," Genbank Accession No. X99718, 19960915.
Kikuti, Y., et al., "*Physical Mapping 220 kb Centromeric of the Human MHC and DNA Sequence Analysis of the 43-kb Segment Including the RING1, HKE6, and HKE4 Genes*," Genbank Accession No. DB84401, 19991120.

*Primary Examiner*—Rebecca E. Prouty
*Assistant Examiner*—Md. Younus Meah
(74) *Attorney, Agent, or Firm*—Bryan Cave LLP

(57) ABSTRACT

The present invention relates to a gene useful in a process to increase the microbial production of carotenoids. The carotenoids astaxanthin is distributed in a wide variety of organisms such as animals, algae and microorganisms. It has a strong antioxidation property against reactive oxygen species. Astaxanthin is used as a coloring reagent, especially in the industry of farmed fish, such as salmon, because astaxanthin imparts distinctive orange-red coloration to the animals and contributes to consumer appeal in the marketplace.

12 Claims, No Drawings

SQS GENE

This application is the National Stage of International Application No. PCT/EP2003/010573, filed Sep. 23, 2003.

The present invention relates to a gene useful in a process to increase the microbial production of carotenoids.

The carotenoid astaxanthin is distributed in a wide variety of organisms such as animals, algae and microorganisms. It has a strong antioxidation property against reactive oxygen species. Astaxanthin is used as a coloring reagent, especially in the industry of farmed fish, such as salmon, because astaxanthin imparts distinctive orange-red coloration to the animals and contributes to consumer appeal in the marketplace.

One of the steps in the carotenogenic pathway of, e.g. *Phaffia rhodozyma*, from a general metabolite, acetyl-CoA is the isomerization of isopentenyl pyrophosphate (IPP) to dimethylaryl pyrophosphate (DMAPP) by the action of IPP isomerase. Then, IPP and DMAPP are converted to a $C_{10}$ unit, geranyl pyrophosphate (GPP) by the head to tail condensation.

In a similar condensation reaction between GPP and IPP, GPP is converted to $C_{15}$ unit, farnesyl pyrophosphate (FPP) which is an important substrate of cholesterol in animal and ergosterol in yeast, and of farnesylation of regulation protein such as RAS protein. In general, the biosynthesis of GPP and FPP from IPP and DMAPP are catalyzed by one enzyme called FPP synthase. On the other hand, in prokaryotes such as eubacteria, isopentenyl pyrophosphate was synthesized in a different pathway via 1-deoxyxylulose-5-phosphate from pyruvate which is absent in yeast and animal. Most of the genes involved in the mevalonate pathway and FPP synthase gene were cloned from *P. rhodozyma* (EP 955,363).

In one aspect, the present invention provides a novel DNA fragment comprising a gene encoding the enzyme squalene synthase.

More particularly, the present invention provides a DNA containing regulatory regions, such as promoter and terminator, as well as the open reading frame of squalene synthase gene.

The present invention provides a DNA fragment encoding squalene synthase in *Phaffia rhodozyma*. The said DNA means a cDNA which contains only open reading frame flanked between the short fragments in its 5'- and 3'-untranslated region, and a genomic DNA which also contains its regulatory sequences such as its promoter and terminator which are necessary for the expression of the squalene synthase gene in *P. rhodozyma*.

Accordingly, the present invention relates to a polynucleotide comprising a nucleic acid molecule selected from the group consisting of:

(a) nucleic acid molecules encoding at least the mature form of the polypeptide depicted in SEQ ID NO:3;

(b) nucleic acid molecules comprising the coding sequence as depicted in SEQ ID NO:2;

(c) nucleic acid molecules whose nucleotide sequence is degenerate as a result of the genetic code to a nucleotide sequence of (a) or (b);

(d) nucleic acid molecules encoding a polypeptide derived from the polypeptide encoded by a polynucleotide of (a) to (c) by way of substitution, deletion and/or addition of one or several amino acids of the amino acid sequence of the polypeptide encoded by a polynucleotide of (a) to (c);

(e) nucleic acid molecules encoding a polypeptide derived from the polypeptide whose sequence has an identity of 51.3% or more to the amino acid sequence of the polypeptide encoded by a nucleic acid molecule of (a) or (b);

(f) nucleic acid molecules comprising a fragment or a epitope-bearing portion of a polypeptide encoded by a nucleic acid molecule of any one of (a) to (e) and having squalene synthase activity;

(g) nucleic acid molecules comprising a polynucleotide having a sequence of a nucleic acid molecule amplified from *Phaffia* or *Xanthophylomyces* nucleic acid library using the primers depicted in SEQ ID NO:4, 5, and 6;

(h) nucleic acid molecules encoding a polypeptide having squalene synthase activity, wherein said polypeptide is a fragment of a polypeptide encoded by any one of (a) to (g);

(i) nucleic acid molecules comprising at least 15 nucleotides of a polynucleotide of any one of (a) to (d);

(j) nucleic acid molecules encoding a polypeptide having squalene synthase activity, wherein said polypeptide is recognized by antibodies that have been raised against a polypeptide encoded by a nucleic acid molecule of any one of (a) to (h);

(k) nucleic acid molecules obtainable by screening an appropriate library under stringent conditions with a probe having the sequence of the nucleic acid molecule of any one of (a) to (j), and encoding a polypeptide having a squalene synthase activity; and (l) nucleic acid molecules whose complementary strand hybridizes under stringent conditions with a nucleic acid molecule of any one of (a) to (k), and encoding a polypeptide having squalene synthase activity.

The terms "gene(s)", "polynucleotide", "nucleic acid sequence", "nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule.

Thus, this term includes double- and single-stranded DNA, and RNA. It also includes known types of modifications, for example, methylation, "caps" substitution of one or more of the naturally occurring nucleotides with an analog. Preferably, the DNA sequence of the invention comprises a coding sequence encoding the above-defined polypeptide.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. SEQ ID:1 depicts the genomic DNA in which the intron sequence is inserted in the coding sequence for squalene synthase gene from *Phaffia rhodozyma*.

In general, the gene consists of several parts which have different functions from each other. In eukaryotes, genes which encode corresponding protein, are transcribed to premature messenger RNA (pre-mRNA) differing from the genes for ribosomal RNA (rRNA), small nuclear RNA (snRNA) and transfer RNA (tRNA). Although RNA polymerase II (PolII) plays a central role in this transcription event, PolII can not solely start transcription without cis element covering an upstream region containing a promoter and an upstream activation sequence (UAS), and a trans-acting protein factor. At first, a transcription initiation complex which consists of several basic protein components recognize the promoter sequence in the 5'-adjacent region of the gene to be expressed. In this event, some additional participants are required in the case of the gene which is expressed under some specific regulation, such as a heat shock response, or adaptation to a nutrition starvation, and so on. In such a case, a UAS is required to exist in the 5'-untranslated upstream region around the promoter sequence, and some positive or negative regulator proteins recognize and bind to the UAS. The strength of the binding of transcription initiation complex to the promoter sequence is affected by such a binding of the trans-acting factor around the promoter, and this enables the regulation of transcription activity.

After the activation of a transcription initiation complex by the phosphorylation, a transcription initiation complex initiates transcription from the transcription start site. Some parts of the transcription initiation complex are detached as an elongation complex from the promoter region to the 3' direction of the gene (this step is called as a promoter clearance event) and the elongation complex continues the transcription until it reaches to a termination sequence that is located in the 3'-adjacent downstream region of the gene. Pre-mRNA thus generated is modified in nucleus by the addition of cap structure at the cap site which almost corresponds to the transcription start site, and by the addition of polyA stretches at the polyA signal which locates at the 3'-adjacent downstream region. Next, intron structures are removed from coding region and exon parts are combined to yield an open reading frame whose sequence corresponds to the primary amino acid sequence of a corresponding protein. This modification in which a mature mRNA is generated is necessary for a stable gene expression. cDNA in general terms corresponds to the DNA sequence which is reverse-transcribed from this mature mRNA sequence. It can be synthesized by the reverse transcriptase derived from viral species by using a mature mRNA as a template, experimentally.

To express a gene which was derived from a eukaryote, a procedure in which cDNA is cloned into an expression vector for *E. coli* is often used. This results from a fact that a specificity of intron structure varies among the organisms and an inability to recognize the intron sequence from other species. In fact, a prokaryote has no intron structure in its own genetic background. Even in yeast, the genetic background is different between *Ascomycetes* to which *Saccharomyces cerevisiae* belongs and *Basidiomycetes* to which *P. rhodozyma* belongs, e.g. the intron structure of actin gene from *P. rhodozyma* cannot be recognized or spliced by the ascomycetous yeast, *Saccharomyces cerevisiae*. The intron structures of some kinds of the genes appear to be involved in the regulation of the expression of their respective gene. It might be important to use a genomic fragment which has its introns in a case of self-cloning of the gene of a interest whose intron structure involves such a regulation of its own gene expression.

To apply a genetic engineering method for a strain improvement study, it is necessary to study its genetic mechanism in the event such as transcription and translation. It is important to determine a genetic sequence such as its UAS, promoter, intron structure and terminator to study the genetic mechanism.

According to this invention, the gene encoding squalene synthase (SQS) gene from *P. rhodozyma* including its 5'- and 3'-adjacent regions as well as its intron structure were determined.

The invention further encompasses polynucleotides that differ from one of the nucleotide sequences shown in SEQ ID NO:2 (and portions thereof) due to degeneracy of the genetic code and thus encode a squalene synthase as that encoded by the nucleotide sequences shown in SEQ ID NO:2. Further the polynucleotide of the invention has a nucleotide sequence encoding a protein having an amino acid sequence shown in SEQ ID NO:3. In a still further embodiment, the polynucleotide of the invention encodes a full length *Phaffia rhodozyma* protein which is substantially homologous to an amino acid sequence of SEQ ID NO:3.

In addition, it will be appreciated by those skilled in the art that DNA sequence polymorphism that lead to changes in the amino acid sequences may exist within a population (e.g., the *P. rhodozyma* population). Such genetic polymorphism in the squalene synthase gene may exist among individuals within a population due to natural variation.

As used herein, the terms "gene" and "recombinant gene" refer to nucleic acid molecules comprising an open reading frame encoding a squalene synthase, preferably a squalene synthase from *P. rhodozyma*.

Such natural variations can typically result in 1-5% variance in the nucleotide sequence of the squalene synthase gene. Any and all such nucleotide variations and resulting amino acid polymorphism in squalene synthase that are the result of natural variation and that do not alter the functional activity of squalene synthase are intended to be within the scope of the invention.

Polynucleotides corresponding to natural variants and non-*P. rhodozyma* homologues of the squalene synthase cDNA of the invention can be isolated based on their homology to *P. rhodozyma* squalene synthase polynucleotides disclosed herein using the polynucleotide of the invention, or a portion thereof, as a hybridization probe according to standard hybridization techniques under stringent hybridization conditions. Accordingly, in another embodiment, a polynucleotide of the invention is at least 15 nucleotides in length.

Preferably it hybridizes under stringent conditions to the nucleic acid molecule comprising a nucleotide sequence of the polynucleotide of the present invention, e.g. SEQ ID NO:2. In other embodiments, the nucleic acid is at least 20, 30, 50, 100, 250 or more nucleotides in length. The term "hybridizes under stringent conditions" is defined above and is intended to describe conditions for hybridization and washing under which nucleotide sequences at least 60% identical to each other typically remain hybridized to each other. Preferably, the conditions are such that sequences at least about 65% or 70%, more preferably at least about 75% or 80%, and even more preferably at least about 85%, 90% or 95% or more identical to each other typically remain hybridized to each other. Preferably, the polynucleotide of the invention that hybridizes under stringent conditions to a sequence of SEQ ID NO:2 corresponds to a naturally occurring nucleic acid molecule.

In the present invention, the polynucleotide sequence includes SEQ ID NO:2 and fragments thereof having polynucleotide sequences which hybridize to SEQ ID NO:2 under stringent conditions which are sufficient to identify specific binding to SEQ ID NO:2. For example, any combination of the following hybridization and wash conditions may be used to achieve the required specific binding:

High Stringent Hybridization: 6×SSC; 0.5% SDS, 100 μg/ml denatured salmon sperm DNA, 50% formamide, incubate overnight with gentle rocking at 42° C.

High Stringent Wash: 1 wash in 2×SSC, 0.5% SDS at room temperature for 15 minutes, followed by another wash in 0.1×SSC, 0.5% SDS at Room Temperature for 15 minutes.

Low Stringent Hybridization: 6×SSC, 0.5% SDS, 100 μg/ml denatured salmon sperm DNA, 50% formamide, incubate overnight with gentle rocking at 37° C.

Low Stringent Wash: 1 wash in 0.1×SSC, 0.5% SDS at room temperature for 15 minutes.

Moderately stringent conditions may be obtained by varying the temperature at which the hybridization reaction occurs and/or the wash conditions as set forth above. In the present invention, it is preferred to use high stringent hybridization and wash conditions to define the antisense activity against squalene synthase gene from *P. rhodozyma*.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations.

These mutations may occur naturally or may be obtained by mutagenesis techniques. The allelic variations may be naturally occurring allelic variants as well as synthetically produced or genetically engineered variants. Structurally equivalents can, for example, identified by testing the binding of said polypeptide to antibodies. Structurally equivalent have the similar immunological characteristic, e.g. comprise similar epitopes.

As used herein, a "naturally-occurring" nucleic acid molecule refers to an RNA or DNA molecule having a nucleotide sequence that occurs in nature (e.g., encodes a natural protein). Preferably, the polynucleotide encodes a natural *P. rhodozyma* squalene synthase.

In addition to naturally-occurring variants of the squalene synthase sequence that may exist in the population, the skilled artisan will further appreciate that changes can be introduced by mutation into a nucleotide sequence of the polynucleotide encoding squalene synthase, thereby leading to changes in the amino acid sequence of the encoded squalene synthase, without altering the functional ability of the squalene synthase. For example, nucleotide substitutions leading to amino acid substitutions at "non-essential" amino acid residues can be made in a sequence of the polynucleotide encoding squalene synthase, e.g. SEQ ID NO:2. A "non-essential" amino acid residue is a residue that can be altered from the wild-type sequence of one of the squalene synthase without altering the activity of said squalene synthase, whereas an "essential" amino acid residue is required for squalene synthase activity. Other amino acid residues, however, (e.g., those that are not conserved or only semi-conserved in the domain having squalene synthase activity) may not be essential for activity and thus are likely to be amenable to alteration without altering squalene synthase activity.

Accordingly, the invention relates to polynucleotides encoding squalene synthase that contain changes in amino acid residues that are not essential for squalene synthase activity. Such squalene synthase differs in amino acid sequence from a sequence contained in SEQ ID NO:3 yet retain the squalene synthase activity described herein. The polynucleotide can comprise a nucleotide sequence encoding a polypeptide, wherein the polypeptide comprises an amino acid sequence at least about 60% identical to an amino acid sequence of SEQ ID NO: 3 and is capable of participation in the synthesis of squalene. Preferably, the protein encoded by the nucleic acid molecule is at least about 60-65% identical to the sequence in SEQ ID NO:3, more preferably at least about 60-70% identical to one of the sequences in SEQ ID NO:3, even more preferably at least about 70-80%, 80-90%, 90-95% homologous to the sequence in SEQ ID NO:3, and most preferably at least about 96%, 97%, 98%, or 99% identical to the sequence in SEQ ID NO:3.

To determine the percent homology of two amino acid sequences (e.g., one of the sequences of SEQ ID NO:3 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO:2 or 3) is occupied by the same amino acid residue or nucleotide as the corresponding position in the other sequence (e.g., a mutant form of the sequence selected), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). The homology can be determined by computer programs as Blast 2.0 (Altschul S F, Nuc. Acid. Res., 25, 3389-3402, 1997). In this invention, GENETYX-SV/RC software (Software Development Co., Ltd., Tokyo, Japan) is used by using its default algorithm as such homology analysis software. This software uses the Lipman-Pearson method for its analytic algorithm.

A nucleic acid molecule encoding a squalene synthase homologous to a protein sequence of SEQ ID NO:3 can be created by introducing one or more nucleotide substitutions, additions or deletions into a nucleotide sequence of the polynucleotide of the present invention, in particular of SEQ ID NO:2 such that one or more amino acid substitutions, additions or deletions are introduced into the encoded protein. Mutations can be introduced into the sequences of, e.g., SEQ ID NO:2 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a squalene synthase is preferably replaced with another amino acid residue from the same family. Alternatively, in another embodiment, mutations can be introduced randomly along all or part of a squalene synthase coding sequence, such as by saturation mutagenesis, and the resultant mutants can be screened for a squalene synthase activity described herein to identify mutants that retain squalene synthase activity. Following mutagenesis of one of the sequences of SEQ ID NO:2, the encoded protein can be expressed recombinantly and the activity of the protein can be determined using, for example, assays described herein.

Accordingly, in one preferred embodiment the polynucleotide of the present invention is DNA or RNA.

A polynucleotide of the present invention, e.g., a nucleic acid molecule having a nucleotide sequence of SEQ ID NO:2, or a portion thereof, can be isolated using standard molecular biology techniques and the sequence information provided herein. For example, squalene synthase cDNA can be isolated from a library using all or portion of one of the sequences of the polynucleotide of the present invention as a hybridization probe and standard hybridization techniques. Moreover, a polynucleotide encompassing all or a portion of one of the sequences of the polynucleotide of the present invention can be isolated by the polymerase chain reaction using oligonucleotide primers designed based upon this sequence (e.g., a nucleic acid molecule encompassing all or a portion of one of the sequences of polynucleotide of the present invention can be isolated by the polymerase chain reaction using oligonucleotide primers, e.g. of SEQ ID NO:4, 5 or 6, designed based upon this same sequence of polynucleotide of the present invention. For example, mRNA can be isolated from cells, e.g. *Phaffia* (e.g., by the guanidinium-thiocyanate extraction procedure of Chirgwin et al., and cDNA can be prepared using reverse transcriptase (e.g., Moloney MLV reverse transcriptase or AMV reverse transcriptase available from Promega (Madison, USA)). Synthetic oligonucleotide primers for polymerase chain reaction amplification can be designed based upon one of the nucleotide sequences shown in SEQ ID NO:2. A polynucleotide of the invention can be amplified using cDNA or, alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to a squalene synthase nucleotide sequence can be prepared by standard synthetic techniques, e.g., using an automated DNA synthesizer.

The terms "fragment", "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence.

Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

The term "one or several amino acids" relates to at least one amino acid but not more than that number of amino acids which would result in a homology of below 60% identity. Preferably, the identity is more than 70% or 80%, more preferred are 85%, 90% or 95%, even more preferred are 96%, 97%, 98%, or 99% identity.

The term "squalene synthase" or "squalene synthase activity" relates to enzymatic activities of a polypeptide as described below or which can be determined in enzyme assay method. Furthermore, polypeptides that are inactive in an assay herein but are recognized by an antibody specifically binding to squalene synthase, i.e., having one or more squalene synthase epitopes, are also comprised under the term "squalene synthase". In these cases activity refers to their immunological activity.

The terms "polynucleotide" and "nucleic acid molecule" also relate to "isolated" polynucleotides or nucleic acids molecules. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived.

For example, in various embodiments, the PNO polynucleotide can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Phaffia* cell). Moreover, the polynucleotides of the present invention, in particular an "isolated" nucleic acid molecule, such as a cDNA molecule, can be substantially free of other cellular material, or culture medium when produced by recombinant techniques, or chemical precursors or other chemicals when chemically synthesized.

Preferably, the polypeptide of the invention comprises one of the nucleotide sequences shown in SEQ ID NO:2. The sequence of SEQ ID NO:2 corresponds to the *P. rhodozyma* squalene synthase cDNAs of the invention.

Further, the polynucleotide of the invention comprises a nucleic acid molecule which is a complement of one of the nucleotide sequences of above mentioned polynucleotides or a portion thereof. A nucleic acid molecule which is complementary to one of the nucleotide sequences shown in SEQ ID NO:2 is one which is sufficiently complementary to one of the nucleotide sequences shown in SEQ ID NO:2 such that it can hybridize to one of the nucleotide sequences shown in SEQ ID NO:2, thereby forming a stable duplex.

The polynucleotide of the invention comprises a nucleotide sequence which is at least about 60%, preferably at least about 65-70%, more preferably at least about 70-80%, 80-90%, or 90-95%, and even more preferably at least about 95%, 96%, 97%, 98%, 99% or more homologous to a nucleotide sequence shown in SEQ ID NO:2, or a portion thereof. The polynucleotide of the invention comprises a nucleotide sequence which hybridizes, e.g., hybridizes under stringent conditions as defined herein, to one of the nucleotide sequences shown in SEQ ID NO:2, or a portion thereof.

Moreover, the polynucleotide of the invention can comprise only a portion of the coding region of one of the sequences in SEQ ID NO:2, for example a fragment which can be used as a probe or primer or a fragment encoding a biologically active portion of a squalene synthase. The nucleotide sequences determined from the cloning of the squalene synthase gene from *P. rhodozyma* allows for the generation of probes and primers designed for use in identifying and/or cloning squalene synthase homologues in other cell types and organisms. The probe/primer typically comprises substantially purified oligonucleotide. The oligonucleotide typically comprises a region of nucleotide sequence that hybridizes under stringent conditions to at least about 12, 15 preferably about 20 or 25, more preferably about 40, 50 or 75 consecutive nucleotides of a sense strand of one of the sequences set forth, e.g., in SEQ ID NO:2, an anti-sense sequence of one of the sequences, e.g., set forth in SEQ ID NO:2, or naturally occurring mutants thereof. Primers based on a nucleotide of invention can be used in PCR reactions to clone squalene synthase homologues. Probes based on the squalene synthase nucleotide sequences can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express a squalene synthase, such as by measuring a level of a squalene synthase-encoding nucleic acid molecule in a sample of cells, e.g., detecting squalene synthase mRNA levels or determining whether a genomic squalene synthase gene has been mutated or deleted.

The polynucleotide of the invention encodes a polypeptide or portion thereof which includes an amino acid sequence which is sufficiently homologous to an amino acid sequence of SEQ ID NO:3 such that the protein or portion thereof maintains the ability to participate in the synthesis of squalene, in particular a squalene synthase activity as described in the examples in microorganisms or plants. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of the polypeptide of the present invention amino acid residues to an amino acid sequence of SEQ ID NO:3 such that the protein or portion thereof is able to participate in the synthesis of squalene in microorganisms or plants. Examples of a squalene synthase activity are also described herein.

The protein is at least about 60-65%, preferably at least about 66-70%, and more preferably at least about 70-80%, 80-90%, 90-95%, and most preferably at least about 96%, 97%, 98%, 99% or more homologous to an entire amino acid sequence of SEQ ID NO:3.

Portions of proteins encoded by the squalene synthase polynucleotide of the invention are preferably biologically active portions of one of the squalene synthase.

As mentioned herein, the term "biologically active portion of squalene synthase" is intended to include a portion, e.g., a domain/motif, that participates in the biosynthesis of squalene or has an immunological activity such that it is binds to an antibody binding specifically to squalene synthase. To determine whether a squalene synthase or a biologically active portion thereof can participate in the metabolism an assay of enzymatic activity may be performed. Such assay methods are well known to those skilled in the art, as detailed in the Examples. Additional nucleic acid fragments encoding biologically active portions of a squalene synthase can be prepared by isolating a portion of one of the sequences in SEQ ID NO:2, expressing the encoded portion of the squalene synthase or peptide (e.g., by recombinant expression in vitro) and assessing the activity of the encoded portion of the squalene synthase or peptide.

At first, a partial gene fragment containing a portion of SQS gene by using degenerate PCR method was cloned. The said degenerate PCR is a method to clone a gene of interest which has high homology of amino acid sequence to the known enzyme from other species which has a same or similar function. Degenerate primer, which is used as a primer in degenerate PCR, was designed by a reverse translation of the amino acid sequence to corresponding nucleotides ("degenerated"). In such a degenerate primer, a mixed primer which consists any of A, C, G or T, or a primer containing inosine at an ambiguity code is generally used. In this invention, such the mixed primers were used for degenerate primers to clone above gene.

An entire gene containing its coding region with its intron as well as its regulation region such as a promoter or a terminator can be cloned from a chromosome by screening of genomic library which is constructed in phage vector or plasmid vector in appropriate host, by using a partial DNA fragment obtained by degenerate PCR as described above as a probe after it was labeled. Generally, *E. coli* as a host strain and *E. coli* vector, a phage vector such as λ phage vector, or a plasmid vector such as pUC vector is often used in the construction of library and a following genetic manipulation such as a sequencing, a restriction digestion, a ligation and the like. In this invention, an EcoRI genomic library of *P. rhodozyma* was constructed in the derivatives of λ vector, λDASHII. An insert size, what length of insert must be cloned, was determined by the Southern blot hybridization for the gene before a construction of a library. In this invention, a DNA used for a probe was labeled with digoxigenin (DIG), a steroid hapten instead of conventional $^{32}P$ label, following the protocol which was prepared by the supplier (Boehringer-Mannheim, Mannheim, Germany). A genomic library constructed from the chromosome of *P. rhodozyma* was screened by using a DIG-labeled DNA fragment which had a portion of a gene of interest as a probe. Hybridized plaques were picked up and used for further study. In the case of using λDASHII (insert size was from 9 kb to 23 kb), prepared λDNA was digested by the EcoRI, followed by the cloning of the EcoRI insert into a plasmid vector such as pUC19 or pBluescriptII SK+. A plasmid DNA thus obtained was examined for its sequence.

In this invention, we used the automated fluorescent DNA sequencer; ALFred system (Pharmacia, Uppsala, Sweden) using an autocycle sequencing protocol in which the Taq DNA polymerase is employed in most cases of sequencing.

After the determination of the genomic sequence, a sequence of a coding region was used for a cloning of cDNA of corresponding gene. The PCR method was also exploited to clone cDNA fragment. The PCR primers whose sequences were identical to the sequence at the 5'- and 3'-end of the open reading frame (ORF) were synthesized with an addition of an appropriate restriction site, and PCR was performed by using those PCR primers. In this invention, a cDNA pool was used as a template in this PCR cloning of cDNA. The said cDNA pool consists of various cDNA species which were synthesized in vitro by the viral reverse transcriptase and Taq polymerase (CapFinder Kit manufactured by Clontech, Palo Alto, U.S.A.) by using the mRNA obtained from *P. rhodozyma* as a template. cDNA of interest thus obtained was confirmed in its sequence.

In another embodiment, the present invention relates to a method for making a recombinant vector comprising inserting a polynucleotide of the invention into a vector.

Further, the present invention relates to a recombinant vector containing the polynucleotide of the invention or produced by said method of the invention.

As used herein, the term "vector" refers to a nucleic acid molecule capable of transporting a polynucleotide to which it has been linked. One type of vector is a "plasmid", which refers to a circular double stranded DNA loop into which additional DNA segments can be ligated. Another type of vector is a viral vector, wherein additional DNA or PNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present invention also relates to cosmids, viruses, bacteriophages and other vectors used conventionally in genetic engineering that contain a nucleic acid molecule according to the invention. Methods which are well known to those skilled in the art can be used to construct various plasmids and vectors. Alternatively, the nucleic acid molecules and vectors of the invention can be reconstituted into liposomes for delivery to target cells.

In an other preferred embodiment to present invention relates to a vector in which the polynucleotide of the present invention is operatively linked to expression control sequences allowing expression in prokaryotic or eukaryotic host cells. The nature of such control sequences differs depending upon the host organism. In prokaryotes, control sequences generally include promoter, ribosomal binding site, and terminators. In eukaryotes, generally control sequences include promoters, terminators and, in some instances, enhancers, transactivators; or transcription factors.

The term "control sequence" is intended to include, at a minimum, components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

Such regulatory sequences are are known to the skilled person. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by polynucleotides as described herein.

The recombinant expression vectors of the invention can be designed for expression of squalene synthase in prokaryotic or eukaryotic cells. For example, genes encoding the polynucleotide of the invention can be expressed in bacterial cells such as *E. coli*, insect cells (using baculovirus expression vectors), yeast and other fungal cells, algae, ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of *Stylonychia lemnae* with vectors following, a transformation method as described in WO 98/01,572 and multicellular plant cells or mammalian cells. Suitable host cells are known to the skilled person. Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc.), pMAL (New England Biolabs, Beverly, USA) and pRIT5 (Pharmacia, Piscataway, USA) which fuse glutathione S-transferase (GST), maltose E binding protein, or protein A, respectively, to the target recombinant protein. In one embodiment, the coding sequence of the polypeptide encoded by the polynucleotide of the present invention is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin, e.g. recombinant squalene synthase unfused to GST can be recovered by cleavage of the fusion protein with thrombin.

Examples of suitable inducible non-fusion *E. coli* expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in host bacteria with an impaired capacity to proteolytically cleave the recombinant protein.

Another strategy is to alter the nucleic acid sequence of the nucleic acid to be inserted into an expression vector so that the individual codons for each amino acid are those preferentially utilized in the bacterium chosen for expression, such as *E. coli*. Such alteration of nucleic acid sequences of the invention can be carried out by standard DNA synthesis techniques.

Further, the squalene synthase vector can be a yeast expression vector. Examples of vectors for expression in yeast *S. cerevisiae* include pYepSec1, pMFa, pJRY88, and pYES2 (Invitrogen, San Diego, USA). Vectors and methods for the construction of vectors appropriate for use in other fungi, such as the filamentous fungi, are known to the skilled person.

Alternatively, the polynucleotide of the invention can be introduced in insect cells using baculovirus expression vectors. Baculovirus vectors available for expression of proteins in cultured insect cells (e.g., Sf9 cells) include the pAc series and the pVL series.

Alternatively, the polynucleotide of the invention is introduced in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, Adenovirus 2, cytomegalovirus and Simian Virus 40. Other suitable expression systems for both prokaryotic and eukaryotic cells are known to the skilled person.

The recombinant mammalian expression vector can be capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific), lymphoid-specific promoters, in particular promoters of T cell receptors and immunoglobulins, neuron-specific promoters (e.g., the neurofilament promoter), pancreas-specific promoters, and mammary gland-specific promoters (e.g., milk whey promoter; U.S. Pat. No. 4,873,316 and EP 264,166). Developmentally-regulated promoters are also encompassed, for example the murine hox promoters and the fetoprotein promoter.

Thus expressed SQS gene can be verified for its activity such as by enzyme assay method. Some experimental protocols are described in the literature. The following is the one of the methods which is used for the determination of squalene synthase activity: squalene synthase activities are determined by monitoring the conversion of $[1-^3H]$ FPP into squalene. Reaction mixtures (500 ml) includes 50 mM Tris-HCl (pH 7.4), 2 mM KF, 1 mM MgCl$_2$, 1 mM NADPH, enzyme, 10 mM $[1-^3H]$ FPP (370 MBq/mmol, 3.7 kBq/mL; New England Nuclear, Boston, Mass.). Reactions are started by adding $[1-^3H]$ FPP. After a 10-min incubation at 37° C., reactions are terminated by adding 1 mL of ethanol. After 1 mL of H$_2$O is added, the mixtures are vigorously shaken with 3 mL of petroleum ether for 30 min. Extracted lipids are evaporated and resuspended in 25 ml of chloroform. Samples are applied to plastic-backed sheets (Silica gel 60, F254; Merck, Rahway, N.J.) for thin-layer chromatography (TLC), and developed in heptane for 15 min. Radioactivities included in the squalene fraction are measured by liquid scintillation counting. When expression vector for *S. cerevisiae* is used, a complementation analysis can be conveniently exploited by using conditional squalene synthase mutant ERG 9 strain derived from *S. cerevisiae* as a host strain for its confirmation of activity (Merkulov et al., Yeast, 16, 197-206, 2000).

Succeeding to the confirmation of the enzyme activity, an expressed protein would be purified and used for raising of the antibody against the purified enzyme. Antibody thus prepared would be used for a characterization of the expression of the corresponding enzyme in a strain improvement study, an optimization study of the culture condition, and the like.

In a further embodiment, the present invention relates to an antibody that binds specifically to the polypeptide of the present invention or parts, i.e. specific fragments or epitopes of such a protein.

The antibodies of the invention can be used to identify and isolate other squalene synthase and genes. These antibodies can be monoclonal antibodies, polyclonal antibodies or synthetic antibodies as well as fragments of antibodies, such as Fab, Fv or scFv fragments etc. Monoclonal antibodies can be prepared, for example, by techniques known to the skilled person, which comprise the fusion of mouse myeloma cells to spleen cells derived from immunized mammals.

Furthermore, antibodies or fragments thereof to the aforementioned peptides can be obtained by using methods which are known to the skilled person. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BlAcore system can be used to increase the efficiency of phage antibodies selections, yielding a high increment of affinity from a single library of phage antibodies which bind to an epitope of the protein of the invention. In many cases, the binding phenomenon of antibodies to antigens is equivalent to other ligand/anti-ligand binding.

In this invention, the gene fragment for squalene synthase was cloned from *P. rhodozyma* with a purpose to decrease its expression level in *P. rhodozyma* by genetic method using the cloned gene fragment.

The present invention provides a process for the production of carotenoids wherein a gene encoding squalene synthase is modified in a suitable host, such as *P. rhodozyma* to decrease its expression, and cultivation of such a transformant in an appropriate medium under appropriate cultivation conditions.

To decrease a gene expression with genetic methods, some strategies can be employed. One of which is a gene-disruption method. In this method, a partial fragment of the objective gene to be disrupted is ligated to a drug resistant cassette on the integration vector which can not replicate in the host organism. A drug resistance gene which encodes the enzyme that enables the host to survive in the presence of a toxic antibiotic is often used for the selectable marker. G418 resistance gene harbored in pGB-Ph9 is an example of a drug resistance gene which functions in *P. rhodozyma*. Nutrition complementation marker can be also used in the host which has an appropriate auxotrophy marker. *P. rhodozyma* ATCC24221 strain that requires cytidine for its growth is one example of the auxotroph. By using CTP synthetase as donor DNA for ATCC24221, a host vector system using a nutrition complementation can be established.

After the transformation of the host organisms and recombination between the objective gene fragment on the vector and its corresponding gene fragment on the chromosome of the host organisms, the integration vector is integrated onto the host chromosome by single cross recombination. As a result of this recombination, the drug resistant cassette would be inserted in the objective gene whose translated product is only synthesized in its truncated form which does not have its enzymatic function. In a similar manner, two parts of the objective gene were also used for gene disruption study in which the drug resistant gene can be inserted between such two partial fragments of the objective genes on the integration vector. In the case of this type of vector, double recombination event between the gene fragments harbored on the integration vector and the corresponding gene fragments on the chromosome of the host are expected. Although frequency of this double crossing-over recombination is lower than single cross recombination, null phenotype of the objective gene by the double cross recombination is more stable than by the single cross recombination.

This strategy was used to construct the lycopene-producing recombinant of *Candida utilis* which harbored bacterial carotenogenic genes on the plasmid (Shimada et al., (Applied and Environmental Microbiology, 64 (7), 2676-2680, 1998)). ERG9 gene encoding squalene synthase was cloned from *C. utilis* and its gene disruptant was induced after double cross recombination of ERG9 gene on the chromosome of the lycopene-producing *C. utilis*. Shimada et al. reported that the disruption of ERG9 gene gave a positive effect on carotenogenesis by the recombinant *C. utilis* especially derived from the host in which 3-hydroxy methylglutaryl-CoA reductase was amplified on the ribosomal DNA locus multi-copied on the chromosome of the host.

On the other hand, this strategy has difficulty in the case of the gene whose function is essential and disruption is lethal for the host organism such as squalene synthase gene. In the above reference (Shimada et al.,), the disruption was made on the either copy of the squalene synthase gene within the two copies of those on the host chromosome. In such a construction, it was not confirmed that the decreased level of the squalene synthase activity was sufficient to increase the carbon flux into the carotenoid pathway.

In such a case, other strategies can be applied to decrease (not to disrupt) a gene expression. One of which is a conventional mutagenesis to screen the mutant whose expression for squalene synthase is decreased. In this method, an appropriate recombinant in which an appropriate reporter gene is fused to the promoter region of squalene synthase gene from the host organism is mutated and mutants which show a weaker activity of reporter gene product can be screened. In such mutants, it is expected that their expression of squalene synthase activity decreased by the mutation lying in the promoter region of reporter gene or trans-acting region which might affect the expression of squalene synthase gene other than the mutation lying in the promoter gene itself. In the case of mutation occurring at the promoter region of the reporter fusion, such mutation can be isolated by the sequence of the corresponding region. Thus isolated mutation can be introduced in a variety of carotenoids, especially astaxanthin producing mutants derived from *P. rhodozyma* by a recombination between the original promoter for squalene synthase gene on the chromosome and the mutated promoter fragment. To exclude mutations occurring at trans-acting region, a mutation can also be induced by an in vitro mutagenesis of a cis element in the promoter region. In this approach, a gene cassette, containing a reporter gene which is fused to a promoter region derived from a gene of interest at its 5'-end and a terminator region from a gene of interest at its 3'-end, is mutagenized and then introduced into *P. rhodozyma*. By detecting the difference of the activity of the reporter gene, an effective mutation can be screened. Such a mutation can be introduced in the sequence of the native promoter region on the chromosome by the same method as the case of an in vivo mutation approach. But, these methods have some drawbacks to have some time-consuming process.

Another strategy to decrease a gene expression is an antisense method. This method is frequently applied to decrease the gene expression even when teleomorphic organisms such as *P. rhodozyma* are used as host organisms, to which the mutation and gene disruption method is usually difficult to be applied. The anti-sense method is a method to decrease an expression of gene of interest by introducing an artificial gene fragment, whose sequence is complementary to cDNA fragment of the gene of interest.

An "antisense" nucleic acid molecule comprises a nucleotide sequence which is complementary to a "sense" nucleic acid molecule encoding a protein, e.g., complementary to the coding strand of a double-stranded cDNA molecule or complementary to a mRNA sequence. Accordingly, an antisense nucleic acid molecule can hydrogen bond to a sense nucleic acid molecule. The antisense nucleic acid molecule can be complementary to an entire squalene synthase-coding strand, or to only a portion thereof. Accordingly, an antisense nucleic acid molecule can be antisense to a "coding region" of the coding strand of a nucleotide sequence encoding a squalene synthase. The term "coding region" refers to the region of the nucleotide sequence comprising codons which are translated into amino acid residues. Further, the antisense nucleic acid molecule is antisense to a "noncoding region" of the coding strand of a nucleotide sequence encoding squalene synthase. The term "noncoding region" refers to 5' and 3' sequences which flank the coding region that are not translated into a polypeptide (i.e., also referred to as 5' and 3' untranslated regions).

Given the coding strand sequences encoding squalene synthase disclosed herein, antisense nucleic acid molecules of the invention can be designed according to the rules of Watson and Crick base pairing. The antisense nucleic acid molecule can be complementary to the entire coding region of squalene synthase mRNA, but can also be an oligonucleotide which is antisense to only a portion of the coding or noncoding region of squalene synthase mRNA. For example, the antisense oligonucleotide can be complementary to the region surrounding the translation start site of squalene synthase mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the anti-sense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-niethylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a polynucleotide has been subcloned in an antisense orientation (i.e., RNA transcribed from the inserted polynucleotide will be of an antisense orientation to a target polynucleotide of interest, described further in the following subsection).

The antisense nucleic acid molecules of the invention are typically administered to a cell or generated in situ such that they hybridize with or bind to cellular mRNA and/or genomic DNA encoding a squalene synthase to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The anti-sense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

Further embodiment, the antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide or a chimeric RNA-DNA analogue.

Further the antisense nucleic acid molecule of the invention can be a ribozyme. Ribozymes are catalytic RNA molecules with ribonuclease activity which are capable of cleaving a single-stranded nucleic acid, such as a mRNA, to which they have a complementary region. Thus, ribozymes (e.g., hammerhead ribozymes) can be used to catalytically cleave squalene synthase mRNA transcripts to thereby inhibit translation of mRNA. A ribozyme having specificity for a squalene synthase-encoding nucleic acid molecule can be designed based upon the polynucleotide sequence of the invention. For example, a derivative of a Tetrahymena L-19 IVS RNA can be constructed in which the nucleotide sequence of the active site is complementary to the nucleotide sequence to be cleaved in an encoding mRNA (U.S. Pat. Nos. 4,987,071 and 5,116,742.) Alternatively, squalene synthase mRNA can be used to select a catalytic RNA having a specific ribonuclease activity from a pool of RNA molecules.

Application of antisense method to construct a carotenoid overproducing strain from P. rhodozyma was exemplified in EP 1,158,051.

In one embodiment the present invention relates to a method of making a recombinant host cell comprising introducing the vector or the polynucleotide of the present invention into a host cell.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells are known to the skilled person.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the polypeptide of the present invention or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of the polynucleotide of the present invention into which a deletion, addition or substitution has been introduced to thereby alter, e.g., functionally disrupt, the squalene synthase gene. Preferably, this squalene synthase gene is a P. rhodozyma squalene synthase gene, but it can be a homologue from a related or different source. Alternatively, the vector can be designed such that, upon homologous recombination, the endogenous squalene synthase gene is mutated or otherwise altered but still encodes functional protein (e.g., the upstream regulatory region can be altered to thereby alter the expression of the endogenous squalene synthase). To create a point mutation via homologous recombination also DNA-RNA hybrids can be used known as chimeraplasty.

The vector is introduced into a cell and cells in which the introduced polynucleotide gene has homologously recombined with the endogenous squalene synthase gene are selected, using art-known techniques.

Further host cells can be produced which contain selection systems which allow for regulated expression of the introduced gene. For example, inclusion of the polynucleotide of the invention on a vector placing it under control of the lac operon permits expression of the polynucleotide only in the presence of IPTG. Such regulatory systems are well known in the art.

Preferably, the introduced nucleic acid molecule is foreign to the host cell.

By "foreign" it is meant that the nucleic acid molecule is either heterologous with, respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination.

Accordingly, in another embodiment the present invention relates to a host cell genetically engineered with the polynucleotide of the invention or the vector of the invention.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

For example, a polynucleotide of the present invention can be introduced in bacterial cells as well as insect cells, fungal cells or mammalian cells (such as Chinese hamster ovary cells (CHO) or COS cells), algae, ciliates, plant cells, fungi or other microorganims like *E. coli*. Other suitable host cells are known to those skilled in the art. Preferred are *E. coli*, baculovirus, *Agrobacterium* or fungal cells are, for example, those of the genus *Saccharomyces*, e.g. those of the species *S. cerevisiae* or *P. rhodozyma* (*Xanthophylomyces dendrorhous*).

In addition, in one embodiment, the present invention relates to a method for the production of fungal transformants comprising the introduction of the polynucleotide or the vector of the present invention into the genome of said fungal cell.

For the expression of the nucleic acid molecules according to the invention in sense or antisense orientation in plant cells, the molecules are placed under the control of regulatory elements which ensure the expression in fungal cells. These regulatory elements may be heterologous or homologous with respect to the nucleic acid molecule to be expressed as well with respect to the fungal species to be transformed.

In general, such regulatory elements comprise a promoter active in fungal cells. To obtain constitutive expression in fungal cells, preferably constitutive promoters are used, such as the glyceraldehyde-3-dehydrogenase promoter from *P. rhodozyma* (WO 97/23,633). Inducible promoters may be used in order to be able to exactly control expression. An example for inducible promoters is the promoter of genes encoding heat shock proteins. Also an amylase gene promoter which is a candidate for such inducible promoters has been described (EP 1,035,206). The regulatory elements may further comprise transcriptional and/or translational enhancers functional in fungal cells. Furthermore, the regulatory elements may include transcription termination signals, such as a poly-A signal, which lead to the addition of a poly A tail to the transcript which may improve its stability.

Methods for the introduction of foreign DNA into fungal cells are also well known in the art. These include, for example, transformation with LiCl method, the fusion of protoplasts, electroporation, biolistic methods like particle bombardment other methods known in the art. Methods for the preparation of appropriate vectors are known to the skilled artisan. Methods for the transformation using biolistic methods are well known to the person skilled in the art.

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid or as chimeric links, or alternatively, may be integrated into the host genome.

In general, the fungi which can be modified according to the invention and which either show overexpression of a protein according to the invention or a reduction of the synthesis of such a protein can be derived from any desired fungal species.

Further, in one embodiment, the present invention relates to a fungal cell comprising the polynucleotide the vector or obtainable by the method of the present invention.

Thus, the present invention relates also to transgenic fungal cells which contain (preferably stably integrated into the genome) a polynucleotide according to the invention linked to regulatory elements which allow expression of the polynucleotide in fungal cells and wherein the polynucleotide is foreign to the transformed fungal cell. For the meaning of foreign see supra.

The presence and expression of the polynucleotide in the transformed fungal cells modulates, preferably decreases the synthesis of squalene and leads to the increase of the carotenoids production, especially astaxanthin production in thus obtained transformed fungal cells; preferably in *P. rhodozyma* cells.

Thus, the present invention also relates to transformed fungal cells according to the invention.

Accordingly, due to the altered expression of squalene synthase, cells metabolic pathways are modulated in yield production, and/or efficiency of production.

The terms "production" or "productivity" are art-recognized and include the concentration of the fermentation product (for example fatty acids, carotenoids, (poly)saccharides, vitamins, isoprenoids, lipids, wax esters, and/or polymers like polyhydroxyalkanoates and/or its metabolism products or further desired fine chemical as mentioned herein) formed within a given time and a given fermentation volume (e.g., kg product/hour/liter).

The term "efficiency" of production includes the time required for a particular level of production to be achieved (for example, how long it takes for the cell to attain a particular rate of output of a said altered yield, in particular, into carotenoids, (poly)saccharides, lipids, vitamins, isoprenoids, etc.).

The term "yield" or "product/carbon yield" is art-recognized and includes the efficiency of the conversion of the carbon source into the product (i.e. acetyl CoA, fatty acids, carotenoids, vitamins, isoprenoids, lipids etc. and/or further compounds as defined above and which biosynthesis is based on said products). This is generally written as, for example, kg product per kg carbon source. By increasing the yield or production of the compound, the quantity of recovered molecules, or of useful recovered molecules of that compound in a given amount of culture over a given amount of time is increased.

The terms "biosynthesis" (which is used synonymously for "synthesis" of "biological production" in cells, tissues plants, etc.) or a "biosynthetic pathway" are art-recognized and include the synthesis of a compound, preferably an organic compound, by a cell from intermediate compounds in what may be a multistep and highly regulated process.

The language "metabolism" is art-recognized and includes the totality of the biochemical reactions that take place in an organism. The metabolism of a particular compound, then, (e.g., the metabolism of acetyl CoA, a fatty acid, hexose, lipid, isoprenoid, vitamin, carotenoid etc.) comprises the overall biosynthetic, modification, and degradation pathways in the cell related to this compound.

Such a genetically engineered *P. rhodozyma* would be cultivated in an appropriate medium and evaluated in its productivity or/and yield of carotenoids, especially astaxanthin. A hyper producer of astaxanthin thus selected would be confirmed in view of the relationship between its productivity and the level of gene or protein expression which is introduced by such a genetic engineering method.

The present invention is further illustrated with Examples described below.

The following materials and methods were employed in the Example described below:

Strains

*P. rhodozyma* ATCC96594 (re-deposited under the accession No. ATCC 74438 on Apr. 8, 1998 pursuant to the Budapest Treaty)

*E. coli* DH5α: F⁻, φ80d, lacZΔM15, Δ(lacZYA-argF) U169, hsd ($r_K^-$, $m_K^+$), recA1, endA1, deoR, thi-1, supE44, gyrA96, relA1 (Toyobo, Osaka, Japan)

*E. coli* XL1 MRA (P2): Δ(mcrA)183, Δ(mcrCB-hsdSMR-mrr)173, endA1, supE44, thi-1, gyrA96, relA1, lac (P2 lysogen) (Stratagene, La Jola, U.S.A.)

Vectors

λDASHII (Stratagene)

pBluescriptII KS-(Stratagene)

pMOSBlue T-vector (Amersham, Buckinghamshire, U.K.)

Media

*P. rhodozyma* strain was maintained routinely in YPD medium (DIFCO, Detroit, U.S.A.).

*E. coli* strain was maintained in LB medium (10 g Bacto-trypton, 5 g yeast extract (DIFCO) and 5 g NaCl per liter). NZY medium (5 g NaCl, 2 g $MgSO_4 \cdot 7H_2O$, 5 g yeast extract (DIFCO), 10 g NZ amine type A (WAKO, Osaka, Japan) per liter) is used for λ phage propagation in a soft agar (0.7% agar (WAKO)). When an agar medium was prepared, 1.5% of agar (WAKO) was supplemented.

Methods

Restriction enzymes and T4 DNA ligase were purchased from Takara Shuzo (Ohtsu, Japan).

Isolation of a chromosomal DNA from *P. rhodozyma* was performed by using QIAGEN Genomic Kit (QIAGEN, Hilden, Germany) following the protocol supplied by the manufacturer. Mini-prep of plasmid DNA from transformed *E. coli* was performed with the Automatic DNA isolation system (PI-50, Kurabo, Co. Ltd., Osaka, Japan). Midi-prep of plasmid DNA from an *E. coli* transformant was performed by using QIAGEN column (QIAGEN). Isolation of λ DNA was performed by Wizard lambda preps DNA purification system (Promega, Madison, U.S.A.) following the protocol prepared by the manufacturer. A DNA fragment was isolated and purified from agarose by using QIAquick or QIAEX II (QIAGEN). Manipulation of λ phage derivatives was followed by the protocol prepared by the manufacturer (Stratagene).

Isolation of total RNA from *P. rhodozyma* was performed with phenol method by using Isogen (Nippon Gene, Toyama, Japan). mRNA was purified from total RNA thus obtained by using mRNA separation kit (Clontech). cDNA was synthesized by using CapFinder cDNA construction kit (Clontech).

In vitro packaging was performed by using Gigapack III gold packaging extract (Stratagene).

Polymerase chain reaction (PCR) is performed with the thermal cycler from Perkin Elmer model 2400. Each PCR condition is described in examples. PCR primers were purchased from a commercial supplier. Fluorescent DNA primers for DNA sequencing were purchased from Pharmacia. DNA sequencing was performed with the automated fluorescent DNA sequencer (ALFred, Pharmacia).

Competent cells of DH5α were purchased from Toyobo (Japan).

EXAMPLE 1

Isolation of mRNA from *P. rhodozyma* and Construction of a cDNA Library

To construct a cDNA library of *P. rhodozyma*, total RNA was isolated by phenol extraction method right after the cell disruption and the mRNA from *P. rhodozyma* ATCC96594 strain was purified by using mRNA separation kit (Clontech).

Cells of strain ATCC96594 from 10 ml of a two-day-culture in YPD medium were harvested by centrifugation (1500×g for 10 min.) and washed once with extraction buffer (10 mM Na-citrate/HCl (pH 6.2) containing 0.7 M KCl). After suspending in 2.5 ml of extraction buffer, the cells were disrupted by French press homogenizer (Ohtake Works Corp., Tokyo, Japan) at 1500 kgf/cm² and immediately mixed with two times of volume of isogen (Nippon gene) according to the method specified by the manufacturer. In this step, 400 μg of total RNA was recovered.

Then, this total RNA was purified by using mRNA separation kit (Clontech) according to the method specified by the manufacturer. Finally, 16 μg of mRNA from *P. rhodozyma* ATCC96594 strain was obtained.

To construct cDNA library, CapFinder PCR cDNA construction kit (Clontech) was used according to the method specified by the manufacturer. One μg of purified mRNA was applied for a first strand synthesis followed by PCR amplification. After this amplification by PCR, 1 mg of cDNA pool was obtained.

EXAMPLE 2

Cloning of a Partial SQS (Squalene Synthase) Gene from *P. rhodozyma*

To clone a partial SQS gene from *P. rhodozyma*, a degenerate PCR method was exploited. Species and accession number to database whose sequence for squalene synthase were used for multiple alignment analysis are as follows.

| | |
|---|---|
| *Ustilago maydis* | Q92459 (SwissProt) |
| *Schizosaccharomyces pombe* | P36596 (SwissProt) |
| *Saccharomyces cerevisiae* | M63979 (GenBank) |
| *Rattus norvegicus* | Q02769 (SwissProt) |
| *Mus musculus* | P53798 (SwissProt) |
| *Candida albicans* | P78589 (SwissProt) |
| *Homo sapiens* | 138245 (Pir) |
| *Arabidopsis thaliana* | U79159, AF004396 |
| *Leishmania major* | U30455 |
| *Glycyrrhiza glabra* | D86410 |

Two mixed primers whose nucleotide sequences were designed and synthesized based on the common sequence of known squalene synthase genes from other species, i.e. squ1 (sense primer) (SEQ ID NO:4), squ4 (antisense primer) (SEQ ID NO:5) and squ5 (anti-sense primer) (SEQ ID NO:6) (in the sequences "n" means nucleotides a, c, g or t, "r" means nucleotides a or g, and "y" means nucleotides c or t).

After the PCR reaction of 25 cycles of 95° C. for 30 seconds, 45° C. for 30 seconds and 72° C. for 15 seconds by using ext. (Takara Shuzo) as a DNA polymerase and cDNA pool obtained in example 1 as a template, the reaction mixture was applied to agarose gel electrophoresis. Each PCR band that had a desired length was recovered from the PCR reaction mixture in which the combination using squ1 and squ4, and squ1 and squ5, respectively and purified by QIAquick (QIAGEN) according to the method by the manufacturer and then ligated to pMOSBlue-T-vector (Amersham). After transformation of competent E. coli DH5α, 6 white colonies were selected and plasmids were isolated with Automatic DNA isolation system. As a result of sequencing, it was found that 3 clones had a sequence whose deduced amino acid sequence was similar to known squalene synthase genes. These isolated cDNA clones were designated as pSQS1007 derived from the PCR reaction using squ1 and squ5 and as pSQS1006 derived from the PCR reaction using squ1 and squ4, and pSQS1006 was used for further screening study.

EXAMPLE 3

Isolation of Genomic DNA from *P. rhodozyma*

To isolate a genomic DNA from *P. rhodozyma*, QIAGEN genomic kit was used according to the method specified by the manufacturer.

Cells of *P. rhodozyma* ATCC96594 from 100 ml of overnight culture in YPD medium were harvested by centrifugation (1500×g for 10 min.) and washed once with TE buffer (10 mM Tris/HCl (pH 8.0) containing 1 mM EDTA). After suspending in 8 ml of Y1 buffer of the QIAGEN genomic kit, lyticase (SIGMA, St. Louis, U.S.A.) was added at the concentration of 2 mg/ml to disrupt cells by enzymatic degradation and the reaction mixture was incubated for 90 minutes at 30° C. and then proceeded to the next extraction step. Finally, 20 μg of genomic DNA was obtained.

EXAMPLE 4

Southern Blot Hybridization by Using pSQS1006 as a Probe

Southern blot hybridization was performed to clone a genomic fragment which contains SQS gene from *P. rhodozyma*. Two μg of genomic DNA was digested by EcoRI and subjected to agarose gel electrophoresis followed by acidic and alkaline treatment. The denatured DNA was transferred to nylon membrane (Hybond N+, Amersham) by using transblot (Joto Rika, Tokyo, Japan) for an hour. The DNA which was transferred to nylon membrane was fixed by a heat treatment (80° C., 90 min). A probe was prepared by labeling a template DNA (EcoRI-digested pSQS1006) with DIG multipriming method (Boehringer Mannheim). Hybridization was performed with the method specified by the manufacturer. As a result, a hybridized band was visualized in the range from 9.0 to 23.0 kilobases (kb).

EXAMPLE 5

Cloning of a Genomic Fragment Containing SQS Gene

Four μg of the genomic DNA was digested by EcoRI and subjected to agarose gel electrophoresis. Then, DNAs whose length is within the range from 9.0 to 20.0 kb was recovered by QIAEX II gel extraction kit (QIAGEN) according to the method specified by the manufacturer. The purified DNA was ligated to 0.5 μg of EcoRI-digested and CIAP (calf intestine alkaline phosphatase)-treated λDASH II (Stratagene) at 16° C. overnight, and packaged by Gigapack III gold packaging extract (Stratagene). The packaged extract was infected to E. coli MRA(P2) strain and over-laid with NZY medium poured onto LB agar medium. About 5000 plaques were screened by using EcoRI-digested pSQS1006 as a probe. Five plaques were hybridized to the labeled probe.

This λDASH II derivative containing putative SQS gene from *P. rhodozyma* was prepared by using Wizard lambda preps DNA purification system (Promega). Next, PCR was conducted by using these λDASH II derivatives as a template and two primers, squ9 and squ10 as primers. These squ 9 and squ10 primers were designed based on the internal sequence of pSQS1006: squ9 (sense primer) (SEQ ID NO:7) and squ10 (antisense primer) (SEQ ID NO:8).

As a result of PCR under the same PCR condition as described in Example 2, an expected 0.5 kb band was yielded. It was suggested that all of those λDASH II derivatives might contain a putative SQS gene from *P. rhodozyma*. Approximately 20.0 kb EcoRI insert fragment in one of these λDASH II derivatives was purified by using QIAEX II (QIAGEN) and subjected to subcloning into pBluescriptII KS-vector (Stratagene) by using DH5α as a host strain and yielded pSQ1229.

EXAMPLE 6

Sequencing of a Genomic Fragment Containing SQS Gene pSQS1229 was sequenced with primer walking procedure by using AutoRead sequencing 15 kit (Pharmacia).

As a result of sequencing, a nucleotide sequence comprising 4807 base pairs of a genomic fragment containing SQS gene from *P. rhodozyma* containing its promoter (1549 bp) and terminator (836 bp) was determined (SEQ ID NO:1).

The coding region was 2422 base pairs long consisting of 9 exons and 8 introns. Introns were dispersed all through the coding region without 5' or 3' bias. It was found that an open reading frame (SEQ ID NO:2) consists of 512 amino acids (SEQ ID NO:3) whose sequence is strikingly similar to the known amino acid sequence of squalene synthase from other species (51.3% identity to squalene synthase from *Schizosaccharomyces pombe*) as a result of homology search by GENETYX-SV/RC software (Software Development Co., Ltd., Tokyo, Japan).

EXAMPLE 7

Construction of Antisense Plasmid for SQS Gene

An antisense gene fragment which covers the entire structure gene for SQS gene is amplified by PCR method and then cloned into integration vector in which antisense SQS gene is transcribed by its own SQS promoter in *P. rhodozyma*.

Such primers include asymmetrical recognition sequence for restriction enzyme, SfiI (GGCCNNNNNGGCC) but their asymmetrical hang-over sequence is designed to be different. This enables a directional cloning into expression vector which has the same asymmetrical sequence at their ligation sequence. The usage of such a construction is exemplified in EP 1,158,051.

For the promoter and terminator fragment which can drive the transcription of the anti-sense SQS gene, SQS promoter and terminator is cloned from the chromosome by using the sequence information listed in SEQ ID NO:1.

Next, SQS terminator fragment is fused to G418 resistant cassette by ligating the DNA fragment containing SQS terminator to G418 resistant cassette of pG418Sa330 (EP 1,035,206) to appropriate vector such as pBluescriptII KS- (Stratagene).

Then, 3.1 kb of SacI fragment containing ribosomal DNA (rDNA) locus (Wery et al., Gene, 184, 89-97, 1997) is inserted in the downstream of G418 cassette on thus prepared plasmid. rDNA fragment exists in multicopies on the chromosome of eukaryote. The integration event via the rDNA fragment would result in multicopied integration onto the chromosome of the host used and this enables the overexpression of foreign genes which are harbored in expression vector.

Subsequently, SQS promoter is inserted in the upstream of SQS terminator to construct of expression vector which functions in *P. rhodozyma*.

Finally, antisense SQS construct is completed by inserting the 1.5 kb of SfiI fragment containing antisense SQS into thus prepared expression vector functioning in *P. rhodozyma*. A similar plasmid construction is exemplified in EP 1,158,051.

EXAMPLE 8

Transformation of *P. rhodozyma* with SQS-Antisense Vector

The SQS-antisense vector thus prepared is transformed into *P. rhodozyma* wild type strain, ATCC96594 by biolistic transformation following the protocol described in EP 1,158, 051.

EXAMPLE 9

Characterization of Antisense SQS Recombinant of *P. rhodozyma*

Antisense SQS recombinant of *P. rhodozyma*, ATCC96594 is cultured in 50 ml of YPD medium in 500 ml Erlenmeyer flask at 20° C. for 3 days by using their seed culture which grows in 10 ml of YPD medium in test tubes (21 mm in diameter) at 20° C. for 3 days. For analysis of carotenoid produced appropriate volume of culture broth is withdrawn and used for analysis of their growth, productivity of carotenoids, especially astaxanthin. For analysis of growth, optical density at 660 nm is measured by using UV-1200 photometer (Shimadzu Corp., Kyoto, Japan) in addition to the determination of their dried cell mass by drying up the cells derived from 1 ml of broth after microcentrifugation at 100° C. for one day.

For analysis of content of astaxanthin and total carotenoids, cells are harvested from 1.0 ml of broth after microcentrifugation and used for the extraction of the carotenoids from cells of *P. rhodozyma* by disruption with glass beads. After extraction, disrupted cells are removed by centrifugation and the resultant is analyzed for carotenoid content with HPLC. The HPLC condition used is as follows: HPLC column; Chrompack Lichrosorb si-60 (4.6 mm, 250 mm); Temperature; room temperature; Eluent; acetone/hexane (18/82) add 1 ml/L of water to eluent; Injection volume; 10 μl; Flow rate; 2.0 ml/minute; Detection; UV at 450 nm.

Reference samples can be obtained from Hoffmann La-Roche (Basel, Switzerland) (particularly astaxanthin) or other commercial suppliers (WAKO, SIGMA, etc.)

The invention claimed is:

1. An isolated polynucleotide sequence selected from the group consisting of a polynucleotide that encodes the polypeptide sequence of SEQ ID NO: 3, a polynucleotide that comprises the sequence of SEQ ID NO: 2, and polynucleotide sequences that are at least 95% identical to the sequence of SEQ ID NO:2 and having squalene synthase activity.

2. The isolated polynucleotide of claim 1, wherein the polynucleotide encodes the polypeptide of SEQ ID NO: 3.

3. The isolated polynucleotide of claim 1, wherein the polynucleotide is SEQ ID NO: 2.

4. The isolated polynucleotide of claim 1, wherein the polynucleotide is at least 95% identical to SEQ ID NO:2 and has squalene synthase activity.

5. The isolated polynucleotide of claim 1, wherein said polynucleotide is isolated from a strain of *Phaffia rhodozyma* or *Xanthophylomyces dendrorhous*.

6. A method for making a recombinant vector comprising inserting the polynucleotide of claim 1 into a vector.

7. A recombinant vector containing the polynucleotide of claim 1.

8. The vector of claim 7 in which the polynucleotide is operatively linked to expression control sequences allowing expression in prokaryotic or eukaryotic cells.

9. A method of making a recombinant microorganism comprising introducing the vector of claim 7 into a host microorganism.

10. The method of claim 9, wherein said host microorganism is selected from *E. coli* and *S. cerevisiae*.

11. A recombinant microorganism containing the vector of claim 7.

12. A process for producing a polypeptide having squalene synthase activity comprising culturing the recombinant microorganism of claim 11 and recovering the polypeptide from the culture of the recombinant microorganism.

* * * * *

SEQUENCE LISTING

```
<160> NUMBER OF SEQ ID NOS: 8

<210> SEQ ID NO 1
<211> LENGTH: 4807
<212> TYPE: DNA
<213> ORGANISM: Phaffia rhodozyma
<220> FEATURE:
<221> NAME/KEY: 5'UTR
<222> LOCATION: (1469)..(1470)
<220> FEATURE:
<221> NAME/KEY: exon
<222> LOCATION: (1550)..(1577)
<220> FEATURE:
<221> NAME/KEY: Intron
<222> LOCATION: (1578)..(1752)
<220> FEATURE:
<221> NAME/KEY: exon
<222> LOCATION: (1753)..(1766)
<220> FEATURE:
<221> NAME/KEY: Intron
<222> LOCATION: (1767)..(1882)
<220> FEATURE:
<221> NAME/KEY: exon
```

```
<222> LOCATION: (1883)..(2071)
<220> FEATURE:
<221> NAME/KEY: Intron
<222> LOCATION: (2072)..(2182)
<220> FEATURE:
<221> NAME/KEY: exon
<222> LOCATION: (2183)..(2397)
<220> FEATURE:
<221> NAME/KEY: Intron
<222> LOCATION: (2398)..(2474)
<220> FEATURE:
<221> NAME/KEY: exon
<222> LOCATION: (2475)..(3087)
<220> FEATURE:
<221> NAME/KEY: Intron
<222> LOCATION: (3088)..(3230)
<220> FEATURE:
<221> NAME/KEY: exon
<222> LOCATION: (3231)..(3356)
<220> FEATURE:
<221> NAME/KEY: Intron
<222> LOCATION: (3357)..(3453)
<220> FEATURE:
<221> NAME/KEY: exon
<222> LOCATION: (3454)..(3475)
<220> FEATURE:
<221> NAME/KEY: Intron
<222> LOCATION: (3476)..(3564)
<220> FEATURE:
<221> NAME/KEY: exon
<222> LOCATION: (3565)..(3881)
<220> FEATURE:
<221> NAME/KEY: Intron
<222> LOCATION: (3882)..(3958)
<220> FEATURE:
<221> NAME/KEY: exon
<222> LOCATION: (3959)..(3970)
<220> FEATURE:
<221> NAME/KEY: polyA_site
<222> LOCATION: (4106)..(4107)

<400> SEQUENCE: 1
gttcctgttc agtcaaagag tgggaaaaac atgaaagtaa aaagatgtaa tgaaagaagg      60
ggtcagaaca tcggagatac aatggcccat agaggaagga aagctactta ccagaaacca     120
gtgaggtttg cctaggaagt aatcccttcg tttctcaaag atatcttttt tgaaagcatc     180
gatgaacgac atgtcgaacc catctccatc ctcgaaatca gtttactcg atttagacct      240 ttccagcttt tctgctctct ccagtttcgc agctttctct cgggaagaa gctctccgcc      300 agtcgatgtt ctgtcgacag gagaccagta gaaggcggaa ccgacaattt tggatggatc    360
ggaggacagg gtggctttaa caaatcggta gtacggagga tcgaacggcg cttctctcgt    420
tcgaaggttg actcctcttg ctatgtgtat gagagcatat ccgttgatgt ctcagttaaa    480
atttcctttt ctttctaccc ggagagtaag acacacaaag aatcacgaag aatatgatga    540
ctgaccgatc cgaatatcta gcgcaggttg cttctctact ggttccattc ttcgaacgat    600
aggttcatgt ttgaaagcat tgatcctagt tgcctctatc tgaggccagt ctgccaatgt    660
agcaggctca atgatcactt ggggtttgtg catcttgatg ttcaaccaag tgtcgcaacg    720
gtcgagattc ttttttcttc ttttggtcga gaaaaaaaa cggcttcgct tcgcacgcgc     780 gcggggatc acccgcatat taagcggtat gacgctcatc aaccggccaa gtgttcttca    840
tcataggtga aggttaaaac ggaatggata ggaggagcta accacgtttt tattttaatt    900
cgacttgggc agcctcgtcc atagtgtctg atggttatat cgtcatagaa aggcagcgcc    960
tggcgggttc gtcatggccg tgatcatctg ctttgttaga cattgtccat cagtcacctc   1020
aatgacagtt tcccgacgcc atcactaaga cacaaacgta tccagcacgc catgtccatc   1080
```

```
                                                       -continued actgaagaag gtagggtctc gtcgagccag tgcaaccaga gttacagatg aacatcaggc    1140
cttgatcaga cccgacttat gaatatggcc gttattgtac acttcttggt gctcctcgag    1200
ctgctctttc gtgtttttca ctttctttcc ggatcaaacg agactgctcg tgtatctatc    1260
tgtgcttgcc atatgagcat cccatgcctc tgctcaaatg atgctggagc tacgatccat    1320
cagagacgac acaaaacggg gttgtatgaa ctctacattt cctaatgtta ttggaatttt    1380
ctgtaatgcg ttcttcatct ttctctaatg cttttttgta gtccgtcttt tcaaccttgc    1440
cagcgtttcg cgtgtcttct ttctcctttg acggtcatca ctttcttctc tcttctcgtt    1500
ctttcttccg tccttccttc tctctcttcg tctgaacatc agcatcatc atg ggc ata    1558
                                                     Met Gly Ile
                                                       1 tca gat tac ctc gtt ctg g gtcagttctg tcttttgttt gattcttatc           1607
Ser Asp Tyr Leu Val Leu
    5 ttcttgccgg cggtcgcctg tcttgggtat atcatcagca atgagaaaca tgatgttccc    1667 cccgcgtcaa tcactgacct tttggtcctc tacttctttc ctgtcgaatt gatcctgatt    1727 gatacgtgtg ccggctgctt aacag ct  ttc acg cat cct gtaggtgttt           1776
                              Ala Phe Thr His Pro
                                   10 tatcgtatgc ttcatgttga tgtttagtca cgcggactga cctggccggt tgattttctg    1836 tatgatcgct tgtgctaccg tctttcttgg aaatccttcc catcag gcc gat ctg       1891
                                                   Ala Asp Leu
                                                        15 cga gct tta atg cag tac gcg atc tgg cat gag cct cga agg aat atc     1939
Arg Ala Leu Met Gln Tyr Ala Ile Trp His Glu Pro Arg Arg Asn Ile
        20                  25                  30 act gca cag gag gaa cat gca aca tcc ggt tgg gac cga gaa act atg     1987
Thr Ala Gln Glu Glu His Ala Thr Ser Gly Trp Asp Arg Glu Thr Met
35                  40                  45 aag gaa tgt tgg aag tat ttg gat ctg act tca aga agt ttc gca gct     2035
Lys Glu Cys Trp Lys Tyr Leu Asp Leu Thr Ser Arg Ser Phe Ala Ala
50                  55                  60                  65 gtc atc aaa gag ttg gac gga gat ctt acc cga gtc gtacgtgttt          2081
Val Ile Lys Glu Leu Asp Gly Asp Leu Thr Arg Val
            70                  75 tcatcttctc tctcctttga gatctggtcg cctccgcatt tcttgttgc agaagggtca    2141 gaagctgaca acaccatctc tactgttcgg gacacggcta g atc tgt tta ttc tat   2197
                                             Ile Cys Leu Phe Tyr
                                                     80 ctc gct ctt cga gga ctg gat acc att gag gat gac atg agt cta tct     2245
Leu Ala Leu Arg Gly Leu Asp Thr Ile Glu Asp Asp Met Ser Leu Ser
        85                  90                  95 aat gat gtg aag ctt ccc ctg ctt cgg aca ttc tgg gaa aag ctt gac     2293
Asn Asp Val Lys Leu Pro Leu Leu Arg Thr Phe Trp Glu Lys Leu Asp
100                 105                 110 tcc cct ggg tgg acc ttt act gga tcc ggt cca aat gag aag gat aga    2341
Ser Pro Gly Trp Thr Phe Thr Gly Ser Gly Pro Asn Glu Lys Asp Arg
115                 120                 125                 130 gag ctt ctt gtt cac ttc gat gtg gcc atc gcc gag ttt gcc aac ttg    2389
Glu Leu Leu Val His Phe Asp Val Ala Ile Ala Glu Phe Ala Asn Leu
            135                 140                 145 gac gtc aa  gtgagtttcc ctttatggtt ggatcatccg ctcgacagac              2437
Asp Val Asn tcgaaacgct catcactttg gtctgcttga tgaacag c tct cgg aac gtc att      2490
                                         Ser Arg Asn Val Ile
```

```
cga gac atc act cgc aag atg ggt aac ggt atg gcc gac ttt gct tct    2538
Arg Asp Ile Thr Arg Lys Met Gly Asn Gly Met Ala Asp Phe Ala Ser
155                 160                 165                 170 ctc tct acg ccc tcc aag cct gtg gcc gag gtc cag tcg acc gaa gat    2586
Leu Ser Thr Pro Ser Lys Pro Val Ala Glu Val Gln Ser Thr Glu Asp
                175                 180                 185 ttc aac cta tac tgt cat tac gtc gct gga ctc gtc ggc gag gga ctc    2634
Phe Asn Leu Tyr Cys His Tyr Val Ala Gly Leu Val Gly Glu Gly Leu
            190                 195                 200 tcc cga ctc ttt gtc gcg acc gag aag gaa cga cca ttc ttg gcc aac    2682
Ser Arg Leu Phe Val Ala Thr Glu Lys Glu Arg Pro Phe Leu Ala Asn
        205                 210                 215 cag atg gta ctt tca aac tcg ttc gga ctc ctt ctc caa aag aca aac    2730
Gln Met Val Leu Ser Asn Ser Phe Gly Leu Leu Leu Gln Lys Thr Asn
    220                 225                 230 atc ctt cga gat att cgg gag gac gcc gac gaa ggt cgt ggc ttc tgg    2778
Ile Leu Arg Asp Ile Arg Glu Asp Ala Asp Glu Gly Arg Gly Phe Trp
235                 240                 245                 250 cca aga gag atc tgg gcc aac ccg atc tat act gcg cat gca ccg ggc    2826
Pro Arg Glu Ile Trp Ala Asn Pro Ile Tyr Thr Ala His Ala Pro Gly
                255                 260                 265 aca agg ttt aac tcg ttg act gac ctg gtc aag aaa gaa aac atc gac    2874
Thr Arg Phe Asn Ser Leu Thr Asp Leu Val Lys Lys Glu Asn Ile Asp
            270                 275                 280 aaa gga tca atg tgg gtg ttg agt gcg atg aca ctc gac gcg atc acc    2922
Lys Gly Ser Met Trp Val Leu Ser Ala Met Thr Leu Asp Ala Ile Thr
        285                 290                 295 cat act acc gac gca ctg gac tac ctc tca ctt cta aag aac cag agt    2970
His Thr Thr Asp Ala Leu Asp Tyr Leu Ser Leu Leu Lys Asn Gln Ser
    300                 305                 310 gtt ttc aac ttt tgt gct atc ccg gct gtc atg tcg att gca acg ttg    3018
Val Phe Asn Phe Cys Ala Ile Pro Ala Val Met Ser Ile Ala Thr Leu
315                 320                 325                 330 gag cta tgc ttc atg aac cca gcg gtg ttc caa cga aac ata aaa atc    3066
Glu Leu Cys Phe Met Asn Pro Ala Val Phe Gln Arg Asn Ile Lys Ile
                335                 340                 345 aga aag gga gaa gcc gtc gag gtgcgttcgc gcgttctgtt tctacctttc      3117
Arg Lys Gly Glu Ala Val Glu
            350 ataacattgg aggttcttga ctcttaagcg tcttccaatc tgatgcctcc aattatcatc   3177 attttgtct tttttgcttt cctcttgttt cttttcggcg tgattcaatc cag ctc       3233
                                                         Leu att atg aag tgc aac aac cct cgg gag gtg gca tac atg ttt aga gat    3281
Ile Met Lys Cys Asn Asn Pro Arg Glu Val Ala Tyr Met Phe Arg Asp
355                 360                 365                 370 tat gct cga aag att cat gcc aag gct att cct aca gat cct aac ttc    3329
Tyr Ala Arg Lys Ile His Ala Lys Ala Ile Pro Thr Asp Pro Asn Phe
                375                 380                 385 atc aag ttg agc gtt gcg tgt ggt cga gtgagttgat cgatcgatcc          3376
Ile Lys Leu Ser Val Ala Cys Gly Arg
            390                 395 atctttgtt ttgatcatcg cgagacttga ctgatcgatt actcaaaaca tcatcgcttc   3436
tccttcttgc tctctag atc gaa caa tgg gct gag cac t gtatgttcct        3485
                Ile Glu Gln Trp Ala Glu His
                400 ccgcccctcc ttcaagtttc ctctcgcttc atctttgttg agaagaggga tctgatgtat  3545
```

-continued

```
ctttctttgt tcggatcag ac tac ccc tca ttt atg atg att cgg cct tcg      3596
                       Tyr Tyr Pro Ser Phe Met Met Ile Arg Pro Ser
                               405                 410 aat gac cct caa aac ccc gca ccc tca acg gcg ctt gac cct ttc tca      3644
Asn Asp Pro Gln Asn Pro Ala Pro Ser Thr Ala Leu Asp Pro Phe Ser
415                 420                 425 gga gac gct cgt tta agg ata gcc tct aag aag gct gag atc acc gcc      3692
Gly Asp Ala Arg Leu Arg Ile Ala Ser Lys Lys Ala Glu Ile Thr Ala
430                 435                 440                 445 gct gct ctt gtc agg aag aaa gcc cgg gat cac gct aag tgg aga gag      3740
Ala Ala Leu Val Arg Lys Lys Ala Arg Asp His Ala Lys Trp Arg Glu
                450                 455                 460 tcc aag gga ttg cct ccg agc gat ccg aac aag ccg gac aac tcg gag      3788
Ser Lys Gly Leu Pro Pro Ser Asp Pro Asn Lys Pro Asp Asn Ser Glu
            465                 470                 475 gat gtt aat tgg gta ttg atc ggc ggt atg atc gtt gga ttg ttg ctc      3836
Asp Val Asn Trp Val Leu Ile Gly Gly Met Ile Val Gly Leu Leu Leu
        480                 485                 490 gtg atg ggc gtg ctc ggt ttg gct atc gct tgg gtt gtt ctt cag          3881
Val Met Gly Val Leu Gly Leu Ala Ile Ala Trp Val Val Leu Gln
    495                 500                 505 gtgcgttctt ccaaagagcc tttctctcat gaacacgcac ataggttgat ctaattctat    3941
cttactctgt catacag ttt gag caa taa tctcaagatt ctagtccatc             3990
                   Phe Glu Gln
                       510 ctttcgctca acgatctgct tcttctcctt tccttctcc gtcttctctg gtttcttttc    4050 ttactttctg ggatcttcct tcttgaatcc tccgatccaa tgtaatctgc ataccctcgc    4110 tttagtagaa accgatcctt cattcgatct tggcgaaaat ctaagcaaag agaatcactt    4170 ttgtctaata aaatttcctt taagagtcg gcttttctt gtggcgaagc ttcatcccgt    4230 cttcctctgg accatctctt ctcaatattc tttgtgctac tatatgatca agttctttga    4290 aatcaaagaa gaacatgtat ttgattttga ggttccaaga atacaaccgg cccaagtcgt    4350 tcttcgcagt tttcatcaga cagcacatat ctctcctcct ctctatagaa gccgtatggg    4410 gccaatcgac tctcatgggt agaccgtgcc cttttgacac ggggagaaag agaacgaaag    4470 gacacttgac cgattcgtta ataaagccgt ccccaccttt tctttaatgg caattcaaga    4530 agagaaaaac aaccctgcg cgcactcgag tagtcgatca gaccttccga acgacagata    4590 tcatttgctg aaatcgaccg gattttaaag ctgctgccag gtcggtgaat ccccctaggt    4650 gatctccttg tacaaagatg ttgggcacgg acttttcgac ccggatgaga acgtcgtgaa    4710 gagtttgaaa aagattatca acataatgtg tcttttttc tttttcttt cgtaactctc    4770 tagagaacga ggagacgtac ggtctgattt gttatcg                             4807

<210> SEQ ID NO 2
<211> LENGTH: 1536
<212> TYPE: DNA
<213> ORGANISM: Phaffia rhodozyma
<220> FEATURE:
<221> NAME/KEY: CDS
<222> LOCATION: (1)..(1536)

<400> SEQUENCE: 2 atg ggc ata tca gat tac ctc gtt ctg gct ttc acg cat cct gcc gat      48
Met Gly Ile Ser Asp Tyr Leu Val Leu Ala Phe Thr His Pro Ala Asp
1               5                  10                  15 ctg cga gct tta atg cag tac gcg atc tgg cat gag cct cga agg aat      96
Leu Arg Ala Leu Met Gln Tyr Ala Ile Trp His Glu Pro Arg Arg Asn
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| atc | act | gca | cag | gag | gaa | cat | gca | aca | tcc | ggt | tgg | gac | cga | gaa | act | 144 |
| Ile | Thr | Ala | Gln | Glu | Glu | His | Ala | Thr | Ser | Gly | Trp | Asp | Arg | Glu | Thr |  |
|  |  |  | 35 |  |  |  | 40 |  |  |  | 45 |  |  |  |  |
| atg | aag | gaa | tgt | tgg | aag | tat | ttg | gat | ctg | act | tca | aga | agt | ttc | gca | 192 |
| Met | Lys | Glu | Cys | Trp | Lys | Tyr | Leu | Asp | Leu | Thr | Ser | Arg | Ser | Phe | Ala |  |
|  |  |  | 50 |  |  |  | 55 |  |  |  | 60 |  |  |  |  |
| gct | gtc | atc | aaa | gag | ttg | gac | gga | gat | ctt | acc | cga | gtc | atc | tgt | tta | 240 |
| Ala | Val | Ile | Lys | Glu | Leu | Asp | Gly | Asp | Leu | Thr | Arg | Val | Ile | Cys | Leu |  |
| 65 |  |  |  |  | 70 |  |  |  |  | 75 |  |  |  |  | 80 |  |
| ttc | tat | ctc | gct | ctt | cga | gga | ctg | gat | acc | att | gag | gat | gac | atg | agt | 288 |
| Phe | Tyr | Leu | Ala | Leu | Arg | Gly | Leu | Asp | Thr | Ile | Glu | Asp | Asp | Met | Ser |  |
|  |  |  |  |  | 85 |  |  |  |  | 90 |  |  |  |  | 95 |  |
| cta | tct | aat | gat | gtg | aag | ctt | ccc | ctg | ctt | cgg | aca | ttc | tgg | gaa | aag | 336 |
| Leu | Ser | Asn | Asp | Val | Lys | Leu | Pro | Leu | Leu | Arg | Thr | Phe | Trp | Glu | Lys |  |
|  |  |  |  | 100 |  |  |  |  | 105 |  |  |  |  | 110 |  |  |
| ctt | gac | tcc | cct | ggg | tgg | acc | ttt | act | gga | tcc | ggt | cca | aat | gag | aag | 384 |
| Leu | Asp | Ser | Pro | Gly | Trp | Thr | Phe | Thr | Gly | Ser | Gly | Pro | Asn | Glu | Lys |  |
|  |  |  | 115 |  |  |  |  | 120 |  |  |  |  | 125 |  |  |  |
| gat | aga | gag | ctt | ctt | gtt | cac | ttc | gat | gtg | gcc | atc | gcc | gag | ttt | gcc | 432 |
| Asp | Arg | Glu | Leu | Leu | Val | His | Phe | Asp | Val | Ala | Ile | Ala | Glu | Phe | Ala |  |
|  |  | 130 |  |  |  |  | 135 |  |  |  |  | 140 |  |  |  |  |
| aac | ttg | gac | gtc | aac | tct | cgg | aac | gtc | att | cga | gac | atc | act | cgc | aag | 480 |
| Asn | Leu | Asp | Val | Asn | Ser | Arg | Asn | Val | Ile | Arg | Asp | Ile | Thr | Arg | Lys |  |
| 145 |  |  |  |  | 150 |  |  |  |  | 155 |  |  |  |  | 160 |  |
| atg | ggt | aac | ggt | atg | gcc | gac | ttt | gct | tct | ctc | tct | acg | ccc | tcc | aag | 528 |
| Met | Gly | Asn | Gly | Met | Ala | Asp | Phe | Ala | Ser | Leu | Ser | Thr | Pro | Ser | Lys |  |
|  |  |  |  | 165 |  |  |  |  | 170 |  |  |  |  | 175 |  |  |
| cct | gtg | gcc | gag | gtc | cag | tcg | acc | gaa | gat | ttc | aac | cta | tac | tgt | cat | 576 |
| Pro | Val | Ala | Glu | Val | Gln | Ser | Thr | Glu | Asp | Phe | Asn | Leu | Tyr | Cys | His |  |
|  |  |  | 180 |  |  |  |  | 185 |  |  |  |  | 190 |  |  |  |
| tac | gtc | gct | gga | ctc | gtc | ggc | gag | gga | ctc | tcc | cga | ctc | ttt | gtc | gcg | 624 |
| Tyr | Val | Ala | Gly | Leu | Val | Gly | Glu | Gly | Leu | Ser | Arg | Leu | Phe | Val | Ala |  |
|  |  | 195 |  |  |  |  | 200 |  |  |  |  | 205 |  |  |  |  |
| acc | gag | aag | gaa | cga | cca | ttc | ttg | gcc | aac | cag | atg | gta | ctt | tca | aac | 672 |
| Thr | Glu | Lys | Glu | Arg | Pro | Phe | Leu | Ala | Asn | Gln | Met | Val | Leu | Ser | Asn |  |
|  | 210 |  |  |  |  | 215 |  |  |  |  | 220 |  |  |  |  |  |
| tcg | ttc | gga | ctc | ctt | ctc | caa | aag | aca | aac | atc | ctt | cga | gat | att | cgg | 720 |
| Ser | Phe | Gly | Leu | Leu | Leu | Gln | Lys | Thr | Asn | Ile | Leu | Arg | Asp | Ile | Arg |  |
| 225 |  |  |  |  | 230 |  |  |  |  | 235 |  |  |  |  | 240 |  |
| gag | gac | gcc | gac | gaa | ggt | cgt | ggc | ttc | tgg | cca | aga | gag | atc | tgg | gcc | 768 |
| Glu | Asp | Ala | Asp | Glu | Gly | Arg | Gly | Phe | Trp | Pro | Arg | Glu | Ile | Trp | Ala |  |
|  |  |  |  | 245 |  |  |  |  | 250 |  |  |  |  | 255 |  |  |
| aac | ccg | atc | tat | act | gcg | cat | gca | ccg | ggc | aca | agg | ttt | aac | tcg | ttg | 816 |
| Asn | Pro | Ile | Tyr | Thr | Ala | His | Ala | Pro | Gly | Thr | Arg | Phe | Asn | Ser | Leu |  |
|  |  |  | 260 |  |  |  |  | 265 |  |  |  |  | 270 |  |  |  |
| act | gac | ctg | gtc | aag | aaa | gaa | aac | atc | gac | aaa | gga | tca | atg | tgg | gtg | 864 |
| Thr | Asp | Leu | Val | Lys | Lys | Glu | Asn | Ile | Asp | Lys | Gly | Ser | Met | Trp | Val |  |
|  |  | 275 |  |  |  |  | 280 |  |  |  |  | 285 |  |  |  |  |
| ttg | agt | gcg | atg | aca | ctc | gac | gcg | atc | acc | cat | act | acc | gac | gca | ctg | 912 |
| Leu | Ser | Ala | Met | Thr | Leu | Asp | Ala | Ile | Thr | His | Thr | Thr | Asp | Ala | Leu |  |
|  | 290 |  |  |  |  | 295 |  |  |  |  | 300 |  |  |  |  |  |
| gac | tac | ctc | tca | ctt | cta | aag | aac | cag | agt | gtt | ttc | aac | ttt | tgt | gct | 960 |
| Asp | Tyr | Leu | Ser | Leu | Leu | Lys | Asn | Gln | Ser | Val | Phe | Asn | Phe | Cys | Ala |  |
| 305 |  |  |  |  | 310 |  |  |  |  | 315 |  |  |  |  | 320 |  |
| atc | ccg | gct | gtc | atg | tcg | att | gca | acg | ttg | gag | cta | tgc | ttc | atg | aac | 1008 |
| Ile | Pro | Ala | Val | Met | Ser | Ile | Ala | Thr | Leu | Glu | Leu | Cys | Phe | Met | Asn |  |
|  |  |  |  | 325 |  |  |  |  | 330 |  |  |  |  | 335 |  |  |
| cca | gcg | gtg | ttc | caa | cga | aac | ata | aaa | atc | aga | aag | gga | gaa | gcc | gtc | 1056 |

-continued

```
                Pro Ala Val Phe Gln Arg Asn Ile Lys Ile Arg Lys Gly Glu Ala Val
                            340                 345                 350 gag ctc att atg aag tgc aac aac cct cgg gag gtg gca tac atg ttt         1104
Glu Leu Ile Met Lys Cys Asn Asn Pro Arg Glu Val Ala Tyr Met Phe
            355                 360                 365 aga gat tat gct cga aag att cat gcc aag gct att cct aca gat cct         1152
Arg Asp Tyr Ala Arg Lys Ile His Ala Lys Ala Ile Pro Thr Asp Pro
370                 375                 380 aac ttc atc aag ttg agc gtt gcg tgt ggt cga atc gaa caa tgg gct         1200
Asn Phe Ile Lys Leu Ser Val Ala Cys Gly Arg Ile Glu Gln Trp Ala
385                 390                 395                 400 gag cac tac tac ccc tca ttt atg atg att cgg cct tcg aat gac cct         1248
Glu His Tyr Tyr Pro Ser Phe Met Met Ile Arg Pro Ser Asn Asp Pro
                405                 410                 415 caa aac ccc gca ccc tca acg gcg ctt gac cct ttc tca gga gac gct         1296
Gln Asn Pro Ala Pro Ser Thr Ala Leu Asp Pro Phe Ser Gly Asp Ala
            420                 425                 430 cgt tta agg ata gcc tct aag aag gct gag atc acc gcc gct gct ctt         1344
Arg Leu Arg Ile Ala Ser Lys Lys Ala Glu Ile Thr Ala Ala Ala Leu
        435                 440                 445 gtc agg aag aaa gcc cgg gat cac gct aag tgg aga gag tcc aag gga         1392
Val Arg Lys Lys Ala Arg Asp His Ala Lys Trp Arg Glu Ser Lys Gly
    450                 455                 460 ttg cct ccg agc gat ccg aac aag ccg gac aac tcg gag gat gtt aat         1440
Leu Pro Pro Ser Asp Pro Asn Lys Pro Asp Asn Ser Glu Asp Val Asn
465                 470                 475                 480 tgg gta ttg atc ggc ggt atg atc gtt gga ttg ttg ctc gtg atg ggc         1488
Trp Val Leu Ile Gly Gly Met Ile Val Gly Leu Leu Leu Val Met Gly
                485                 490                 495 gtg ctc ggt ttg gct atc gct tgg gtt gtt ctt cag ttt gag caa taa         1536
Val Leu Gly Leu Ala Ile Ala Trp Val Val Leu Gln Phe Glu Gln
            500                 505                 510

<210> SEQ ID NO 3
<211> LENGTH: 511
<212> TYPE: PRT
<213> ORGANISM: Phaffia rhodozyma

<400> SEQUENCE: 3

Met Gly Ile Ser Asp Tyr Leu Val Leu Ala Phe Thr His Pro Ala Asp
1               5                   10                  15

Leu Arg Ala Leu Met Gln Tyr Ala Ile Trp His Glu Pro Arg Arg Asn
            20                  25                  30

Ile Thr Ala Gln Glu Glu His Ala Thr Ser Gly Trp Asp Arg Glu Thr
        35                  40                  45

Met Lys Glu Cys Trp Lys Tyr Leu Asp Leu Thr Ser Arg Ser Phe Ala
    50                  55                  60

Ala Val Ile Lys Glu Leu Asp Gly Asp Leu Thr Arg Val Ile Cys Leu
65                  70                  75                  80

Phe Tyr Leu Ala Leu Arg Gly Leu Asp Thr Ile Glu Asp Asp Met Ser
                85                  90                  95

Leu Ser Asn Asp Val Lys Leu Pro Leu Leu Arg Thr Phe Trp Glu Lys
            100                 105                 110

Leu Asp Ser Pro Gly Trp Thr Phe Thr Gly Ser Gly Pro Asn Glu Lys
        115                 120                 125

Asp Arg Glu Leu Leu Val His Phe Asp Val Ala Ile Ala Glu Phe Ala
    130                 135                 140

Asn Leu Asp Val Asn Ser Arg Asn Val Ile Arg Asp Ile Thr Arg Lys
```

```
            145                 150                 155                 160
Met Gly Asn Gly Met Ala Asp Phe Ala Ser Leu Ser Thr Pro Ser Lys
                165                 170                 175

Pro Val Ala Glu Val Gln Ser Thr Glu Asp Phe Asn Leu Tyr Cys His
            180                 185                 190

Tyr Val Ala Gly Leu Val Gly Glu Gly Leu Ser Arg Leu Phe Val Ala
        195                 200                 205

Thr Glu Lys Glu Arg Pro Phe Leu Ala Asn Gln Met Val Leu Ser Asn
    210                 215                 220

Ser Phe Gly Leu Leu Gln Lys Thr Asn Ile Leu Arg Asp Ile Arg
225                 230                 235                 240

Glu Asp Ala Asp Glu Gly Arg Gly Phe Trp Pro Arg Glu Ile Trp Ala
                245                 250                 255

Asn Pro Ile Tyr Thr Ala His Ala Pro Gly Thr Arg Phe Asn Ser Leu
            260                 265                 270

Thr Asp Leu Val Lys Lys Glu Asn Ile Asp Lys Gly Ser Met Trp Val
        275                 280                 285

Leu Ser Ala Met Thr Leu Asp Ala Ile Thr His Thr Thr Asp Ala Leu
    290                 295                 300

Asp Tyr Leu Ser Leu Leu Lys Asn Gln Ser Val Phe Asn Phe Cys Ala
305                 310                 315                 320

Ile Pro Ala Val Met Ser Ile Ala Thr Leu Glu Leu Cys Phe Met Asn
                325                 330                 335

Pro Ala Val Phe Gln Arg Asn Ile Lys Ile Arg Lys Gly Glu Ala Val
            340                 345                 350

Glu Leu Ile Met Lys Cys Asn Asn Pro Arg Glu Val Ala Tyr Met Phe
        355                 360                 365

Arg Asp Tyr Ala Arg Lys Ile His Ala Lys Ala Ile Pro Thr Asp Pro
    370                 375                 380

Asn Phe Ile Lys Leu Ser Val Ala Cys Gly Arg Ile Glu Gln Trp Ala
385                 390                 395                 400

Glu His Tyr Tyr Pro Ser Phe Met Met Ile Arg Pro Ser Asn Asp Pro
                405                 410                 415

Gln Asn Pro Ala Pro Ser Thr Ala Leu Asp Pro Phe Ser Gly Asp Ala
            420                 425                 430

Arg Leu Arg Ile Ala Ser Lys Lys Ala Glu Ile Thr Ala Ala Ala Leu
        435                 440                 445

Val Arg Lys Lys Ala Arg Asp His Ala Lys Trp Arg Glu Ser Lys Gly
    450                 455                 460

Leu Pro Pro Ser Asp Pro Asn Lys Pro Asp Asn Ser Glu Asp Val Asn
465                 470                 475                 480

Trp Val Leu Ile Gly Gly Met Ile Val Gly Leu Leu Leu Val Met Gly
                485                 490                 495

Val Leu Gly Leu Ala Ile Ala Trp Val Val Leu Gln Phe Glu Gln
            500                 505                 510

<210> SEQ ID NO 4
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: n = a, c, g or t
```

-continued

```
<220> FEATURE:
<221> NAME/KEY: misc_feature
<222> LOCATION: (4)..(4)
<223> OTHER INFORMATION: y = c or t
<220> FEATURE:
<221> NAME/KEY: misc_feature
<222> LOCATION: (6)..(6)
<223> OTHER INFORMATION: n = a, c, g or t
<220> FEATURE:
<221> NAME/KEY: misc_feature
<222> LOCATION: (12)..(12)
<223> OTHER INFORMATION: n = a, c, g or t
<220> FEATURE:
<221> NAME/KEY: misc_feature
<222> LOCATION: (15)..(15)
<223> OTHER INFORMATION: n = a, c, g or t

<400> SEQUENCE: 4
gcnytngaya cngtngarga ygayatg                                          27

<210> SEQ ID NO 5
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: n = a, c, g or t
<220> FEATURE:
<221> NAME/KEY: misc_feature
<222> LOCATION: (9)..(9)
<223> OTHER INFORMATION: n = a, c, g or t
<220> FEATURE:
<221> NAME/KEY: misc_feature
<222> LOCATION: (15)..(15)
<223> OTHER INFORMATION: n = a, c, g or t
<220> FEATURE:
<221> NAME/KEY: misc_feature
<222> LOCATION: (18)..(18)
<223> OTHER INFORMATION: n = a, c, g or t
<220> FEATURE:
<221> NAME/KEY: misc_feature
<222> LOCATION: (21)..(21)
<223> OTHER INFORMATION: n = a, c, g or t

<400> SEQUENCE: 5
atngccatna cytgnggnat ngcrca                                           26

<210> SEQ ID NO 6
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: n = a, c, g or t
<220> FEATURE:
<221> NAME/KEY: misc_feature
<222> LOCATION: (6)..(6)
<223> OTHER INFORMATION: n = a, c, g or t
<220> FEATURE:
<221> NAME/KEY: misc_feature
<222> LOCATION: (9)..(9)
<223> OTHER INFORMATION: n = a, c, g or t
<220> FEATURE:
<221> NAME/KEY: misc_feature
<222> LOCATION: (12)..(12)
<223> OTHER INFORMATION: n = a, c, g or t
<220> FEATURE:
<221> NAME/KEY: misc_feature
<222> LOCATION: (15)..(15)
```

```
<223> OTHER INFORMATION: n = a, c, g or t

<400> SEQUENCE: 6
ccnacngtnc cngcnacrta rtgrcarta                              29

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
aatgatgtga agcttcccct                                        20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
ccagatctct cttggccaga                                        20
```